United States Patent [19]

Rybak et al.

[11] Patent Number: 5,716,612
[45] Date of Patent: Feb. 10, 1998

[54] USE OF IL-4 FOR POTENTIATION OF CHEMOTHERAPEUTIC AGENTS

[75] Inventors: Mary Ellen M. Rybak, Warren, N.J.; Bertrand Coiffier, Lyons, France

[73] Assignee: Schering Corporation, Kenilworth, N.J.

[21] Appl. No.: 321,504

[22] Filed: Oct. 12, 1994

Related U.S. Application Data

[63] Continuation-in-part of Ser. No. 301,929, Sep. 7, 1994, abandoned.

[51] Int. Cl.$^6$ .................................................. A61K 45/05
[52] U.S. Cl. ................................................................. 424/85.2
[58] Field of Search .......................................... 424/85.2

[56] References Cited

U.S. PATENT DOCUMENTS

| | | | |
|---|---|---|---|
| 4,958,007 | 9/1990 | Alroy et al. | 530/351 |
| 5,246,700 | 9/1993 | Yamaguchi et al. | 424/85.2 |
| 5,382,427 | 1/1995 | Plunkett et al. | 424/85.2 |

FOREIGN PATENT DOCUMENTS

| | | |
|---|---|---|
| WO 87/02990 | 5/1987 | WIPO. |
| WO 91/06655 | 5/1991 | WIPO. |

OTHER PUBLICATIONS

Toi et al., *Cancer Res.*, vol. 52, pp. 275–279, 1992.
O'Shaughnessy et al., *JAMA*, vol. 270(17), pp. 2089–2092, 1993.
Neidhert, *Cancer suppl.*, vol. 72(11), pp. 3381–3386, 1993.
Tepper et al., *Cell*, vol. 57, pp. 503–512, 1989.
DeFrance, et al., *J. Immunol.* 141, (No. 6) 2000–2005 (1988).
Butler, et al., *J. Immunol.*, 133, (No. 1) 251–255 (1984).
Rennick, et al., *Immunology*, 84, 6889–6893 (1987).
Yokota, et al., *Biochemistry*, 83, 5894–5898 (1986).
Mosmann, et al., *Immunology*, 83, 5654–5658 (1986).
Ohara, et al., *J. Immunol.*, 135, (No. 4) 2518–2523 (1985).
Sanderson, et al., *Immunology*, 83, 437–440 (1986).
Rabin, et al., *Immunology*, 82, 2935–2939 (1985).
Noelle, et al., *Immunology*, 81, 6149–6153 (1984).
Farrar, et al., *J. Immunol.*, 131, (No. 4) 1838–1842 (1983).
Karray, et al., *J. Exp. Med.*, 168, 85–94 (1988).
Hu–Li, et al., *J. Exp. Med.*, 165, 157–172 (1987).
Crawford, et al., *J. Immunol.*, 139, (No. 1) 135–141 (1987).
Fernandez–Botran, et al., *J. Exp. Med.*, 164, 580–595 (1986).
Grabstein, et al., *Exp. Med.*, 163, 1405–1414 (1986).
Tepper, et al., *Cell*, 57, 503–512 (1989).
Mosmann, *J. Immunol. Meth.*, 65, 55–63 (1983).

*Primary Examiner*—Chhaya D. Sayala
*Attorney, Agent, or Firm*—Norman C. Dulak; Paul A. Thompson; Immac J. Thampoe

[57] ABSTRACT

Described is a method for potentiating the effects of chemotherapeutic agents or radiation therapy in mammals afflicted with cancer. The method comprises administering IL-4 in conjunction either with other chemotherapeutic agents or with radiation therapy.

8 Claims, No Drawings

USE OF IL-4 FOR POTENTIATION OF CHEMOTHERAPEUTIC AGENTS

This application is a continuation-in-part of co-owned U.S. Ser. No. 08/301,929, filed Sep. 7, 1994 abandoned.

The present invention relates to a method for potentiating the effects of chemotherapeutic agents in mammals by administering to said mammals an effective amount of interleukin-4.

BACKGROUND OF THE INVENTION

Interleukin-4 (IL-4) is a cytokine having pleiotropic effects on B-lymphocyte cells. Krammer, et al., *Proc. Nat. Acad. Sci. USA*, 81, 6149–6153 (1984), discloses that in vitro IL-4 increases surface class II major histocompatibility antigens. IL-4 can also improve B cell viability [Rabin, et al., *Proc. Nat. Acad. Sci. USA*, 82, 2935–2939 (1985)] and induce expression of $Fc_\epsilon$ receptors. Human IL-4 has been shown to stimulate production of IgG and IgM, Defrance, et al., *J. Immunol.*, (1988). IL-4 also inhibits proliferation of selected B cell populations and can counteract IL-2-induced proliferation of monoclonal chronic lymphocytic leukemia cells in vitro. See, Karrau, et al., *J. Exp. Med.*, 168, 85–94 (1988); Rennick, et al., *Proc. Nat. Acad. USA*, 84, 6889–6893 (1987).

The effects of IL-4 have been demonstrated on other cell types as well. IL-4 can increase the viability and stimulate growth of normal helper and suppressor T cells [Hu-Li, et al., *J. Exp. Med.*, 165, 157 (1987)] and T cell lines [Mosmann, et al., *Proc. Nat. Acad. Sci. USA*, 83, 5654 (1986), Fernandez-Botran, et al., *J. Exp. Med.*, 164, 580 (1986)]. IL-4 also stimulates nonspecific macrophage cytotoxicity and enhances the ability of macrophages to present antigen, Crawford, et al., *J. Immunol.*, 139, 135 (1987). In addition, studies reported in Tepper, et al., *Cell*, 57, 503–512 (1989), suggest that murine IL-4 displays potent anti-tumor activity in vivo.

Chemotherapeutic agents are frequently used for the treatment of patients with leukemia, lymphomas, myelomas, certain carcinomas, and other types of cancers. However, some patients are resistant to chemotherapy, i.e., do not respond to initial chemotherapy. Others suffer relapse of disease following initial chemotherapy and develop resistance to chemotherapeutic agents following repeated treatment.

For example, the treatment of patients with Hodgkin's Disease or non-Hodgkin's lymphoma generally involves combination chemotherapy, which can achieve remission rates as high as 80% in patients with stage III or stage IV Hodgkin's Disease. However, patients who achieve remission are at risk of relapse as resistance to the chemotherapy develops.

Treatment of lymphoma patients suffering from relapse and those who are resistant generally requires high dose combination chemotherapy in conjunction with autologous bone marrow transplants. Such treatment can result in remission, but remissions under these circumstances are not as frequent or durable as remission obtained through initial combination chemotherapy in previously untreated patients. Consequently there is a need for a method of treating relapsing or resistant cancer patients, and in particular for treating relapsing or resistant Hodgkin's Disease and non-Hodgkin's lymphoma patients.

Other forms of treatment for cancer are also known in the art, such as radiation therapy. However, some patients are resistant to radiation therapy, i.e., do not respond to radiation therapy. Consequently there is also a need for a method of treating cancer patients who are resistant to other types of cancer therapy, such as radiation therapy.

SUMMARY OF THE INVENTION

The present invention fills the foregoing need by providing a method for treating mammals afflicted with cancer which results in sensitization of the mammals to treatment with other chemotherapeutic agents.

More particularly, the present invention provides in one embodiment a method for potentiating the effects of chemotherapeutic agents comprising administering an effective amount of IL-4 to a mammal afflicted with cancer, in conjunction with one or more other chemotherapeutic agents.

This invention further provides a method for potentiating the effects of chemotherapeutic agents comprising:
(a) administering an effective amount of IL-4 to a mammal afflicted with cancer, which has become resistant to one or more other chemotherapeutic agents, for a period sufficient to induce sensitivity to the other chemotherapeutic agents; and
(b) reinstituting treatment of said mammals with the other chemotherapeutic agents.

In a preferred embodiment, the mammal is a human being afflicted with Hodgkin's Disease or non-Hodgkin's lymphoma.

In an alternative embodiment, the present invention provides a method for treating mammals afflicted with cancer which results in sensitization of the mammals to other forms of treatment, such as radiation therapy.

More particularly, the present invention provides a method for potentiating the effects of radiation therapy comprising administering an effective amount of IL-4 to a mammal afflicted with cancer, in conjunction with radiation therapy.

DETAILED DESCRIPTION

All references cited herein are hereby incorporated in their entirety by reference.

As used herein, the term "potentiating the effects of chemotherapeutic agents" means increasing the effectiveness of said agents for the treatment of cancer in a mammal. Similarly, the term "potentiating the effects of radiation therapy" means increasing the effectiveness of said therapy for the treatment of cancer in a mammal.

"Increased effectiveness" is determined by detecting an improvement in the anti-cancer activity of a specified dosage regimen of either the chemotherapeutic agents when administered following, or concurrently with, an effective amount of IL-4 as compared to administration of the same dosage of chemotherapeutic agents without IL-4. Typically, increased effectiveness is demonstrated where a mammal shows little or no response to chemotherapy prior to IL-4 treatment, and an improved response to chemotherapy either following IL-4 treatment or when co-administered with IL-4. The increased effectivenss of radiation therapy in conjunction with IL-4 treatment is determined by substantially the same method.

A "resistant mammal" is herein defined as a mammal which has demonstrated resistance to chemotherapeutic agents as determined by the absence of favorable results following chemotherapy. Preferably the resistant mammal is a human being, and in a particularly preferred embodiment, a resistant mammal is a resistant or recurrent Hodgkin's Disease or non-Hodgkins lymphoma patient, as defined below.

Administration of IL-4 in "conjunction with one or more other chemotherapeutic agents" means that the IL-4 is administered either (a) prior to the start of chemotherapy, (b) prior to the resumption of chemotherapy where chemotherapy has been stopped or suspended, or (c) during the course of chemotherapy, i.e., concurrently with administration of other chemotherapeutic agents.

A variety of therapeutic agents are known for administration to patients in need of chemotherapy, including: 1,3-bis(2-chloroethyl)-1-nitrosourea [BiCNU], bleomycin sulfate, 5-fluorouracil, 6-mercaptopurine, prednisone, methotrexate, lomustine, mitomycin, cisplatin, procarbazine hydrochloride, dacarbazine, cytarabine, streptozocin, epipodophyllotoxin, etoposide [VP-16], taxol, anthracycline antibiotics such as doxorubicin hydrochloride (adriamycin) and mitoxantrone, vinca alkaloids such as vinblastine sulfate and vincristine sulfate, and alkylating agents such as mechlorethamine, cyclophosphamide and ifosfamide. These agents are typically used alone or in combination chemotherapy for the treatment of neoplastic diseases, as described in *The Merck Manual*, 16th Ed., R. Berkow, ed., Merck Research Laboratories (Rahway, N.J. 1992).

In particular, for the treatment of Hodgkin's Disease preferred chemotherapeutic agents include combination therapy with: mechlorethamine, vincristine, procarbazine and prednisone; or adriamycin, bleomycin, vinblastine and dacarbazine. Preferred combinations for treatment of non-Hodgkin's lymphoma include: cyclophosphamide, vincristine, and prednisone, with or without adriamycin; or the combination of those four agents with drugs such as bleomycin, methotrexate, cytarabine and procarbazine.

Chemotherapy is used in the treatment of a variety of cancers. As used herein the term "cancer" includes lymphomas, carcinomas and sarcomas, and other neoplastic conditions, as these terms are commonly used in the art. See, e.g. *The Merck Manual*, 16th Ed., supra. The method of the present invention can be used for the potentiation of chemotherapeutic agents in patients having such diseases who are resistant to said agents.

In the particular cases of Hodgkin's Disease or non-Hodgkin's lymphoma, patients may be resistant to chemotherapy, or may exhibit reduced sensitivity to such agents upon recurrence of the disease following chemotherapy induced remission. The increased effectiveness of chemotherapeutic agents induced by IL-4 treatment is determined in such patients by detection of favorable results, as defined below, upon resumption of chemotherapy following IL-4 treatment.

Administration of IL-4 in "conjunction with radiation therapy" means that the IL-4 is administered either (a) prior to the start of radiation therapy, (b) prior to the resumption of radiation therapy where such therapy has been stopped or suspended, or (c) during the course of radiation therapy, i.e., concurrently with administration of such therapy.

Methods for the treatment of cancer using radiation therapy are well known in the art. See, e.g. *The Merck Manual*, 16th Ed., supra.

Typically, resistant or recurrent patients are those who have progressive disease after two different chemotherapy regimens or those who have not responded after at least two cycles of a second chemotherapy schedule.

"Favorable results" are herein defined as either a partial or complete response to chemotherapy. In determining such responses, all measurable lesions must be addressed with no new lesions or disease related symptoms detected.

"Complete response" is defined as the substantially complete disappearance of all evidence of disease. In the case of Hodgkin's Disease or non-Hodgkin's lymphoma, complete response is also evinced by negative bilateral bone marrow aspiration and biopsy.

"Partial response" is defined as a measurable regression of disease that amounts to less than complete response. In the case of Hodgkin's Disease or non-Hodgkin's lymphoma, partial response is a greater than or equal to 50% decrease under baseline in the sum of products of perpendicular diameters of all measurable lesions.

Any suitable IL-4 may be employed in the present invention. Mammalian IL-4 can be made by standard recombinant DNA methods, such as described in U.S. Pat. No. 5,017,691. In addition, human and murine IL-4 can be purchased from commercial sources, such as Genzyme Corporation, Boston, Mass. Moreover, non-recombinant IL-4 has been purified from various culture supernatants, e.g. Sanderson, et al., *Proc. Nat. Acad. Sci. USA*, 83, 437–440 (1986), (mouse); Grabstein, et al., *J. Exp. Med.*, 163, 1405–1413 (1985), (mouse); Ohara, et al., *J. Immunol.*, 135, 2518–2523 (1985), (mouse BSF-1); Butler, et al., *J. Immunol.*, 133, 251–255 (1984), (human BCGF); and Farrar, et al., *J. Immunol.*, 131, 1838–1842 (1983), (mouse BCGF).

Preferably, the IL-4 used in the present invention is human IL-4 when human beings are being treated. Most preferred is recombinant human IL-4 produced in secretory *E. coli* strains as described in PCT international Application No. PCT/US89/04788, and recombinant human IL-4 having the sequence described in Yokota, et al., *Proc. Nat. Acad. Sci. USA*, 83, 5894–5898 (1986) and PCT International Application No. PCT/US87/02990.

According to this invention, mammals are administered an effective amount of an IL-4 for a period sufficient to potentiate the effects of chemotherapeutic agents, or to sensitize previously resistant patients to the anti-tumor effects of chemotherapy. The dosage range will typically be from about 0.20 µg to about 25 µg of IL-4 per kg of body weight per day. Preferably, mammals are administered about 0.25 µg to about 10 µg of recombinant hIL-4 (rhIL-4) per kg of body weight per day, and most preferably mammals are administered about 0.25 µg to about 5 µg of rhIL-4 per kilogram of body weight per day.

The amount, frequency and period of administration will vary depending upon factors such as the level of the neutrophil and monocyte count (e.g., the severity of the monocytopenia or granulocytopenia), age of the patient, nutrition, etc. Preferably the administration of IL-4 will be daily initially and may continue periodically during the patient's lifetime. Dosage amount and frequency may be determined during initial screenings of neutrophil count and the magnitude of the effect of IL-4 upon the increase in antibody levels.

Administration of the dose can be intravenous, parenteral, subcutaneous, intramuscular, or any other acceptable systemic method, with subcutaneous administration being preferred. The IL-4 can be administered in any number of conventional dosage forms. Parenteral preparations include sterile solutions or suspensions. Dosages of more than about 10 to about 25 micrograms of recombinant IL-4 per kilogram of body weight are preferably intravenously administered to human beings.

The formulations of pharmaceutical compositions contemplated by the above dosage forms can be prepared with conventional pharmaceutically acceptable excipients and additives, using conventional techniques, such as those described in *Remington's Pharmaceutical Sciences* 18th Ed., A. Gennaro, ed., Mack Publishing Co. (Easton, Pa. 1990).

Presently, the IL-4 is preferably administered systemically, preferably via subcutaneous or intraperitoneal injection or even intravenous injection. The solutions to be administered may be reconstituted lyophilized powders and they may additionally contain preservatives, buffers, dispersants, etc.

Preferably, IL-4 is reconstituted with sterile water or 10 millimolar citrate buffer and preservative-free sterile water with the maximum concentration not to exceed 100 micrograms per milliliter and administered systemically via subcutaneous injection, intraperitoneal injection or via continuous intravenous infusion or by intravenous injection. For continuous infusion, the daily dose can be added to 5 ml of normal saline and the solution infused by mechanical pump or by gravity.

The present invention can be illustrated by the following examples, but this invention is not to be construed as limited thereby.

EXAMPLES

Materials and Methods

Recombinant hIL-4 obtained from Schering-Plough Corporation (Union, N.J.) is used at the indicated concentrations. Schering's rhIL-4 is greater than 95% pure and has a specific activity of approximately $2 \times 10^7$ units/mg of protein. Specific activity can be determined via suitable assays procedures such as those described in Mosmann, *J. Immunol. Methods*, 65, 55–63 (1983).

The rhIL-4 is obtained as a sterile powder in 25 μg and 100 μg vials (containing a total of 30 μg or 120 μg of rhIL-4, respectively). The rhIL-4 is reconstituted by addition of 1.2 mL of Sterile Water for Injection USP to the vial to give 1.2 mL of a solution containing 25 μg or 100 μg of rhIL-4 per mL. The reconstituted solution is stored at 2° to 8° C. until use and is used within 24 hours of reconstitution.

Treatment of Hodgkin's Disease

A total of 24 patients having histologically demonstrated recurrent or resistant Hodgkin's Disease, as defined herein, were selected for treatment with IL-4. All patients had measurable disease as defined by a mass at least 2 cm×2 cm in two perpendicular diameters by physical examination, chest X-ray, CT scan or positive bone marrow aspiration and biopsy. All chemotherapy and/or radiation therapy was stopped at least 4 weeks prior to the start of IL-4 treatments, and no radiation therapy or chemotherapeutic agents were administered during the course of treatment with IL-4.

Patients were treated with a 1.0 μg/kg dose of rhIL-4, administered daily. The rhIL-4 was administered via subcutaneous injection and treatments were continued for a period of 8 weeks.

Following conclusion of IL-4 therapy, the patients were again treated with chemotherapeutic agents for a period of 1–3 months. Combinations of chemotherapeutic agents were used, including anthracyclines, vinca alkaloids and alkylating agents. Five of the 24 patients exhibited favorable responses to chemotherapy as evinced by either partial or complete response, as defined above.

In assessing patient response, all measurable lesions were addressed, and for patients exhibiting a favorable response no new lesions detected. "Complete response" was confirmed by disappearance of all evidence of disease including negative bilateral bone marrow aspiration and biopsy.

Treatment of Non-Hodgkin's Lymphoma

Three patients having histologically demonstrated recurrent or resistant non-Hodgkin's lymphoma were selected for treatment with IL-4. The patients were selected, treated and evaluated following substantially the same protocols as defined above for Hodgkin's Disease patients, but at a dosage of 5 μg/kg per day.

Following conclusion of IL-4 therapy, the patients were again treated with chemotherapeutic agents using substantially the same protocol as described above for Hodgkin's disease patients. One of the 3 patients exhibited favorable responses to chemotherapy as defined by either partial or complete response.

Modifications and variations of the present invention can be made without departing from its spirit and scope, as will become apparent to one of ordinary skill in the art. The specific embodiments described herein are offered by way of example only and the invention should not be construed as limited thereby.

We claim:

1. A method for potentiating the effects of chemotherapeutic agents comprising:

(a) administering an effective amount of IL-4 to a mammal afflicted with a cancer which has become resistant to one or more other chemotherapeutic agents, for a period sufficient to induce sensitivity of the cancer to the other chemotherapeutic agent(s); and (b) reinstituting treatment of said mammals with the other chemotherapeutic agent(s).

2. The method of claim 1 wherein the mammal is a human being.

3. The method of claim 2 wherein the human being is afflicted with Hodgkin's Disease or non-Hodgkin's lymphoma.

4. The method of claim 3 wherein the IL-4 is human IL-4.

5. The method of claim 4 wherein the human IL-4 is recombinant human IL-4.

6. The method of claim 5 wherein the IL-4 is administered daily for a period of about 8 weeks before reinstating treatment with said chemotherapeutic agents.

7. A method for potentiating the effects of radiation therapy comprising:

(a) administering an effective amount of IL-4 to a mammal afflicted with cancer which has become resistant to radiation therapy, for a period sufficient to induce sensitivity of the cancer to radiation therapy; and (b) reinstituting treatment of said mammals with radiation therapy.

8. The method of claim 7 wherein the mammal is a human being.

* * * * *